(12) United States Patent
Caparso et al.

(10) Patent No.: US 11,883,667 B2
(45) Date of Patent: Jan. 30, 2024

(54) BIASED NEUROMODULATION LEAD AND METHOD OF USING SAME

(71) Applicant: XII Medical, Inc., Cleveland, OH (US)

(72) Inventors: Anthony V. Caparso, North Ridgeville, OH (US); Josh Nickols, Louisville, KY (US)

(73) Assignee: XII Medical, Inc., Cleveland, OH (US)

( * ) Notice: Subject to any disclaimer, the term of this patent is extended or adjusted under 35 U.S.C. 154(b) by 0 days.

(21) Appl. No.: 17/660,042

(22) Filed: Apr. 21, 2022

(65) Prior Publication Data

US 2022/0241588 A1 Aug. 4, 2022

Related U.S. Application Data

(62) Division of application No. 16/865,668, filed on May 4, 2020, now Pat. No. 11,420,061.

(60) Provisional application No. 62/915,194, filed on Oct. 15, 2019.

(51) Int. Cl.
*A61N 1/36* (2006.01)
*A61N 1/372* (2006.01)

(52) U.S. Cl.
CPC ........ *A61N 1/3611* (2013.01); *A61N 1/37229* (2013.01)

(58) Field of Classification Search
CPC .. A61N 1/3611; A61N 1/3601; A61N 1/3606; A61N 1/36057; A61N 1/0551; A61N 1/3605; A61N 1/0548; A61N 1/0558; A61N 1/36; A61N 1/36189; A61B 5/4818; A61B 2562/164; A61B 5/0031; A61B 5/682; A61B 5/4519; A61B 5/4836; A61B 5/0826; A61B 5/04; A61B 5/04001; A61B 5/686; A61B 5/00; A61B 5/4815
See application file for complete search history.

(56) References Cited

U.S. PATENT DOCUMENTS

| | | |
|---|---|---|
| 4,990,160 A | 2/1991 | Terino |
| 5,335,657 A | 8/1994 | Terry et al. |
| 5,522,862 A | 6/1996 | Testerman et al. |
| 5,591,216 A | 1/1997 | Testerman et al. |

(Continued)

FOREIGN PATENT DOCUMENTS

| | | |
|---|---|---|
| JP | 2013208182 A | 10/2013 |
| WO | 92/19318 A1 | 11/1992 |

(Continued)

OTHER PUBLICATIONS

Bailey, "Activities of human genioglossus motor units", Respiratory Physiology & Neurobiology 179:14-22, 2011.

(Continued)

*Primary Examiner* — Deborah L Malamud
(74) *Attorney, Agent, or Firm* — Fortem IP LLP; Candice Hsu; Katrina Marcelo

(57) ABSTRACT

A neuromodulation lead that is biased towards a substantially omega shape when fully deployed is provided. The neuromodulation lead includes a left set of electrodes disposed on a left portion of the lead body of the neuromodulation lead and a right set of electrodes disposed on a right portion of the lead body of the neuromodulation lead. The neuromodulation lead can be positioned in the plane between the genioglossus muscle and the geniohyoid muscle.

29 Claims, 9 Drawing Sheets

(56) References Cited

U.S. PATENT DOCUMENTS

| | | |
|---|---|---|
| 5,609,621 A | 3/1997 | Bonner |
| 5,716,377 A | 2/1998 | Rise et al. |
| 5,877,466 A | 3/1999 | Bolongeat-Mobleu et al. |
| 5,988,171 A | 11/1999 | Sohn et al. |
| 6,240,316 B1 | 5/2001 | Richmond et al. |
| 6,314,324 B1 | 11/2001 | Lattner et al. |
| 6,587,725 B1 | 7/2003 | Durand et al. |
| 6,770,022 B2 | 8/2004 | Mechlenburg et al. |
| 7,660,632 B2 | 2/2010 | Kirby et al. |
| 7,668,591 B2 | 2/2010 | Lee et al. |
| 7,711,438 B2 | 5/2010 | Lettner et al. |
| 7,885,713 B2 | 2/2011 | Campbell et al. |
| 8,204,602 B2 | 6/2012 | Kallmyer |
| 8,255,056 B2 | 8/2012 | Tehrani |
| 8,498,712 B2 | 7/2013 | Bolea et al. |
| 8,498,713 B2 | 11/2013 | Mashiach |
| 8,574,164 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,577,647 B2 | 11/2013 | Farritor et al. |
| 8,585,617 B2 | 11/2013 | Mashiach et al. |
| 8,588,941 B2 | 11/2013 | Mashiach |
| 8,626,304 B2 | 1/2014 | Bolea et al. |
| 8,644,957 B2 | 2/2014 | Mashiach |
| 8,700,183 B2 | 4/2014 | Mashiach |
| 8,718,776 B2 | 5/2014 | Mashiach et al. |
| 8,744,589 B2 | 6/2014 | Bolea et al. |
| 8,798,773 B2 | 6/2014 | Meadows et al. |
| 8,812,113 B2 | 8/2014 | Mashiach |
| 8,812,135 B2 | 8/2014 | Mashiach |
| 8,831,730 B2 | 9/2014 | Mashiach et al. |
| 8,838,256 B2 | 9/2014 | Mashiach et al. |
| 8,897,880 B2 | 11/2014 | Mashiach |
| 8,897,895 B2 | 11/2014 | Mashiach |
| 8,903,493 B2 | 12/2014 | Mashiach et al. |
| 8,903,515 B2 | 12/2014 | Mashiach |
| 8,948,871 B2 | 2/2015 | Mashiach et al. |
| 8,958,893 B2 | 2/2015 | Mashiach |
| 8,989,868 B2 | 3/2015 | Mashiach et al. |
| 9,031,653 B2 | 5/2015 | Mashiach |
| 9,031,654 B2 | 5/2015 | Meadows et al. |
| 9,044,612 B2 | 6/2015 | Mashiach et al. |
| 9,061,151 B2 | 6/2015 | Mashiach et al. |
| 9,061,162 B2 | 6/2015 | Mashiach et al. |
| 9,095,725 B2 | 8/2015 | Mashiach |
| 9,101,774 B2 | 8/2015 | Mashiach et al. |
| 9,155,899 B2 | 10/2015 | Mashiach et al. |
| 9,186,511 B2 | 11/2015 | Bolea |
| 9,220,907 B2 | 12/2015 | Mashiach et al. |
| 9,220,908 B2 | 12/2015 | Mashiach |
| 9,248,290 B2 | 2/2016 | Mashiach |
| 9,248,302 B2 | 2/2016 | Mashiach et al. |
| 9,259,585 B2 | 2/2016 | Vajha et al. |
| 9,302,093 B2 | 4/2016 | Mashiach |
| 9,308,370 B2 | 4/2016 | Lima et al. |
| 9,308,381 B2 | 4/2016 | Mashiach et al. |
| 9,314,613 B2 | 4/2016 | Mashiach |
| 9,314,641 B2 | 4/2016 | Meadows et al. |
| 9,327,132 B2 | 5/2016 | Mashiach |
| 9,339,651 B2 | 5/2016 | Meadows et al. |
| 9,358,392 B2 | 6/2016 | Mashiach |
| 9,370,657 B2 | 6/2016 | Tehrani et al. |
| 9,393,435 B2 | 7/2016 | Mashiach |
| 9,403,009 B2 | 8/2016 | Mashiach |
| 9,403,025 B2 | 8/2016 | Mashiach et al. |
| 9,409,013 B2 | 8/2016 | Mashiach et al. |
| 9,415,215 B2 | 8/2016 | Mashiach |
| 9,415,216 B2 | 8/2016 | Mashiach |
| 9,421,372 B2 | 8/2016 | Mashiach et al. |
| 9,463,318 B2 | 10/2016 | Mashiach et al. |
| 9,486,628 B2 | 11/2016 | Christopherson et al. |
| 9,757,560 B2 | 9/2017 | Papay |
| 9,849,288 B2 | 12/2017 | Meadows et al. |
| 9,950,166 B2 | 4/2018 | Mashiach et al. |
| 10,029,098 B2 | 7/2018 | Papay |
| 10,065,038 B2 | 9/2018 | Papay |
| 10,105,538 B2 | 10/2018 | Bolea et al. |
| 10,238,468 B2 | 3/2019 | Forsell |
| 10,675,467 B2 | 6/2020 | Papay |
| 11,291,842 B2 | 4/2022 | Caparso et al. |
| 11,338,142 B2 | 5/2022 | Papay |
| 11,351,377 B2 | 6/2022 | Papay et al. |
| 11,351,380 B2 | 6/2022 | Caparso et al. |
| 11,420,061 B2 | 8/2022 | Caparso et al. |
| 11,420,063 B2 | 8/2022 | Caparso et al. |
| 11,491,333 B2 | 11/2022 | Papay |
| 11,691,010 B2 | 7/2023 | Caparso et al. |
| 11,771,899 B2 | 10/2023 | Papay et al. |
| 2002/0010495 A1 | 1/2002 | Freed et al. |
| 2004/0122787 A1 | 6/2004 | Avinash et al. |
| 2006/0224211 A1 | 10/2006 | Durand et al. |
| 2007/0160274 A1 | 7/2007 | Mashiach |
| 2007/0239230 A1 | 10/2007 | Giftakis et al. |
| 2007/0263915 A1 | 11/2007 | Mashiach |
| 2008/0039904 A1 | 2/2008 | Beutler et al. |
| 2008/0260229 A1 | 10/2008 | Mashiach |
| 2009/0082831 A1 | 3/2009 | Paul et al. |
| 2009/0226057 A1 | 9/2009 | Mashiach et al. |
| 2009/0270960 A1 | 10/2009 | Zhao et al. |
| 2010/0094379 A1 | 4/2010 | Meadows et al. |
| 2010/0179562 A1 | 7/2010 | Linker et al. |
| 2010/0241195 A1 | 9/2010 | Meadows et al. |
| 2010/0260217 A1 | 10/2010 | Redford |
| 2010/0280568 A1 | 11/2010 | Bulkes et al. |
| 2010/0292769 A1 | 11/2010 | Brounstein et al. |
| 2011/0071606 A1 | 3/2011 | Kast et al. |
| 2011/0093032 A1 | 4/2011 | Boggs et al. |
| 2011/0093036 A1 | 4/2011 | Mashiach |
| 2011/0137376 A1 | 6/2011 | Meskens |
| 2011/0230702 A1 | 9/2011 | Honour |
| 2012/0010532 A1 | 1/2012 | Bolea et al. |
| 2012/0010681 A1 | 1/2012 | Bolea et al. |
| 2013/0085537 A1 | 4/2013 | Mashiach |
| 2013/0085558 A1 | 4/2013 | Mashiach |
| 2013/0204097 A1 | 8/2013 | Rondoni et al. |
| 2013/0289401 A1 | 10/2013 | Colbaugh et al. |
| 2014/0031840 A1 | 1/2014 | Mashiach |
| 2014/0031902 A1 | 1/2014 | Mashiach |
| 2014/0031903 A1 | 1/2014 | Mashiach |
| 2014/0031904 A1 | 1/2014 | Mashiach |
| 2014/0046221 A1 | 2/2014 | Mashiach et al. |
| 2014/0052219 A1 | 2/2014 | Mashiach et al. |
| 2014/0100642 A1 | 4/2014 | Mashiach |
| 2014/0135868 A1 | 5/2014 | Bashyam |
| 2014/0172061 A1 | 6/2014 | Mashiach |
| 2014/0266933 A1 | 9/2014 | Andersen et al. |
| 2014/0358026 A1 | 12/2014 | Mashiach et al. |
| 2014/0358189 A1 | 12/2014 | Mashiach et al. |
| 2014/0358196 A1 | 12/2014 | Mashiach |
| 2014/0358197 A1 | 12/2014 | Mashiach et al. |
| 2014/0371802 A1 | 12/2014 | Mashiach et al. |
| 2014/0371817 A1 | 12/2014 | Mashiach et al. |
| 2014/0379049 A1 | 12/2014 | Mashiach et al. |
| 2015/0032177 A1 | 1/2015 | Mashiach et al. |
| 2015/0073232 A1 | 3/2015 | Ahmad et al. |
| 2015/0077308 A1 | 3/2015 | Jeon et al. |
| 2015/0088025 A1 | 3/2015 | Litvak et al. |
| 2015/0096167 A1 | 4/2015 | Zhao et al. |
| 2015/0112402 A1 | 4/2015 | Mashiach |
| 2015/0112416 A1 | 4/2015 | Mashiach et al. |
| 2015/0142120 A1 | 5/2015 | Papay |
| 2015/0224307 A1 | 8/2015 | Bolea |
| 2015/0265221 A1 | 9/2015 | Flanagan et al. |
| 2015/0283313 A1 | 10/2015 | Huber |
| 2015/0290465 A1 | 10/2015 | Mashiach |
| 2015/0343221 A1 | 12/2015 | Mashiach |
| 2016/0094082 A1 | 3/2016 | Ookawa et al. |
| 2016/0106976 A1 | 4/2016 | Kucklick |
| 2016/0121121 A1 | 5/2016 | Mashiach |
| 2016/0121122 A1 | 5/2016 | Mashiach |

(56) References Cited

U.S. PATENT DOCUMENTS

| | | | |
|---|---|---|---|
| 2016/0175587 A1 | 6/2016 | Lima et al. |
| 2016/0184583 A1 | 6/2016 | Meadows et al. |
| 2016/0235990 A1 | 8/2016 | Mashiach |
| 2016/0346537 A1 | 12/2016 | Mashiach |
| 2017/0087360 A1 | 3/2017 | Scheiner |
| 2017/0128002 A1 | 5/2017 | Christopherson et al. |
| 2017/0143257 A1 | 5/2017 | Kent et al. |
| 2017/0143280 A1 | 5/2017 | Kent et al. |
| 2017/0290699 A1 | 10/2017 | Radmand |
| 2018/0015282 A1 | 1/2018 | Waner et al. |
| 2018/0028824 A1 | 2/2018 | Pivonka et al. |
| 2018/0117313 A1 | 5/2018 | Schmidt et al. |
| 2018/0191069 A1 | 7/2018 | Chen et al. |
| 2018/0280694 A1* | 10/2018 | Mashiach ............ A61N 1/3756 |
| 2019/0117966 A1 | 4/2019 | Kent |
| 2019/0151656 A1 | 5/2019 | Bolea et al. |
| 2019/0160282 A1 | 5/2019 | Dieken et al. |
| 2019/0247664 A1 | 8/2019 | Yazoqui et al. |
| 2020/0016401 A1 | 1/2020 | Papay et al. |
| 2020/0254249 A1 | 8/2020 | Rondoni et al. |
| 2020/0269044 A1 | 8/2020 | Papay |
| 2020/0346010 A1 | 11/2020 | Papay et al. |
| 2020/0346016 A1 | 11/2020 | Caparso et al. |
| 2020/0346017 A1 | 11/2020 | Caparso et al. |
| 2020/0346024 A1 | 11/2020 | Caparso et al. |
| 2021/0128914 A1 | 5/2021 | Papay |
| 2022/0218988 A1 | 7/2022 | Caparso et al. |
| 2022/0266030 A1 | 8/2022 | Caparso et al. |
| 2022/0288390 A1 | 9/2022 | Papay et al. |
| 2022/0323752 A1 | 10/2022 | Papay |
| 2022/0370798 A1 | 11/2022 | Caparso et al. |
| 2022/0401738 A1 | 12/2022 | Caparso et al. |
| 2023/0024498 A1 | 1/2023 | Caparso et al. |
| 2023/0277843 A1 | 9/2023 | Caparso et al. |
| 2023/0310860 A1 | 10/2023 | Papay |

FOREIGN PATENT DOCUMENTS

| | | | |
|---|---|---|---|
| WO | 2005/018737 A1 | 3/2005 |
| WO | 2007/080579 A2 | 7/2007 |
| WO | 2007/080580 A2 | 7/2007 |
| WO | 2007080579 A3 | 7/2007 |
| WO | 2007080580 A3 | 7/2007 |
| WO | 2008/129545 A1 | 10/2008 |
| WO | 2009/007896 A2 | 1/2009 |
| WO | 2009007896 A3 | 1/2009 |
| WO | 2009/109971 A2 | 9/2009 |
| WO | 2009109971 A3 | 9/2009 |
| WO | 2009/143560 A1 | 12/2009 |
| WO | 2010/006218 A2 | 1/2010 |
| WO | 2011/048590 A1 | 4/2011 |
| WO | 2011/077433 A1 | 6/2011 |
| WO | 2013/046032 A2 | 4/2013 |
| WO | 2013/046035 A2 | 4/2013 |
| WO | 2013/046038 A2 | 4/2013 |
| WO | 2013/046039 A2 | 4/2013 |
| WO | 2013/046040 A2 | 4/2013 |
| WO | 2013/046042 A2 | 4/2013 |
| WO | 2013/046043 A2 | 4/2013 |
| WO | 2013/046044 A2 | 4/2013 |
| WO | 2013/046048 A2 | 4/2013 |
| WO | 2013/046049 A2 | 4/2013 |
| WO | 2013/046053 A2 | 4/2013 |
| WO | 2013/057594 A2 | 4/2013 |
| WO | 2013046032 A3 | 4/2013 |
| WO | 2013046035 A3 | 4/2013 |
| WO | 2013046038 A3 | 4/2013 |
| WO | 2013046039 A3 | 4/2013 |
| WO | 2013046040 A3 | 4/2013 |
| WO | 2013046042 A3 | 4/2013 |
| WO | 2013046043 A3 | 4/2013 |
| WO | 2013046044 A3 | 4/2013 |
| WO | 2013046048 A3 | 4/2013 |
| WO | 2013046049 A3 | 4/2013 |
| WO | 2013046053 A3 | 4/2013 |
| WO | 2013057594 A3 | 4/2013 |
| WO | 2013/061164 A2 | 5/2013 |
| WO | 2013/061169 A2 | 5/2013 |
| WO | 2013061164 A3 | 5/2013 |
| WO | 2013061169 A3 | 5/2013 |
| WO | 2013/177621 A1 | 12/2013 |
| WO | 2014/016684 A2 | 1/2014 |
| WO | 2014/016686 A2 | 1/2014 |
| WO | 2014/016687 A2 | 1/2014 |
| WO | 2014/016688 A2 | 1/2014 |
| WO | 2014/016691 A2 | 1/2014 |
| WO | 2014/016692 A2 | 1/2014 |
| WO | 2014/016693 A2 | 1/2014 |
| WO | 2014/016694 A2 | 1/2014 |
| WO | 2014/016697 A2 | 1/2014 |
| WO | 2014/016700 A2 | 1/2014 |
| WO | 2014/016701 A2 | 1/2014 |
| WO | 2014016684 A3 | 1/2014 |
| WO | 2014016686 A3 | 1/2014 |
| WO | 2014016687 A3 | 1/2014 |
| WO | 2014016688 A3 | 1/2014 |
| WO | 2014016691 A3 | 1/2014 |
| WO | 2014016692 A3 | 1/2014 |
| WO | 2014016693 A3 | 1/2014 |
| WO | 2014016694 A3 | 1/2014 |
| WO | 2014016697 A3 | 1/2014 |
| WO | 2014016700 A3 | 1/2014 |
| WO | 2014016701 A3 | 1/2014 |
| WO | 2014/047310 A1 | 3/2014 |
| WO | 2014/049448 A2 | 4/2014 |
| WO | 2014/057361 A2 | 4/2014 |
| WO | 2014049448 A3 | 4/2014 |
| WO | 2014057361 A3 | 4/2014 |
| WO | 2014/096969 A2 | 6/2014 |
| WO | 2014/096971 A2 | 6/2014 |
| WO | 2014/096973 A2 | 6/2014 |
| WO | 2014096969 A3 | 6/2014 |
| WO | 2014096973 A3 | 6/2014 |
| WO | 2014/207576 A2 | 12/2014 |
| WO | 2014207576 A3 | 12/2014 |
| WO | 2015/004540 A2 | 1/2015 |
| WO | 2015004540 A3 | 1/2015 |
| WO | 2015/139053 A1 | 9/2015 |
| WO | 2017112960 A1 | 6/2017 |
| WO | 2017/173433 A1 | 10/2017 |
| WO | 2022155632 A1 | 7/2022 |

OTHER PUBLICATIONS

Björninen, Toni, et al., "The Effect of Fabrication Method on Passive UHF RFID Tag Performance", International Journal of Antennas and Propagation, https://doi.org/10.1155/2009/920947, 2009, 8 pages.

Bjorninen, T. et al., "The effect of fabrication method on passive UHF RFID tag performance", 2009, International Journal of Antennas and Propagation, vol. 2009, Article ID 920947, pp. 1-8.

Bailey, "Activities of human genioglossus motor units", 2011, Respiratory Physiology & Neurobiology 179:14-22.

Cienfuegos et al., Mandible—Surgical approach—Intraocular—AO Surgery Reference, v1 .0 Dec. 1, 2008—(Accessed Apr. 18, 2016).

Cienfuegos et al., Mandible—Surgical approach—Submental—AO Surgery Reference, v1 .0 Dec. 1, 2008—(Accessed Apr. 18, 2016).

Schwartz, A.R. et al., "Electrical stimulation of the lingual musculature in obstructive sleep apnea", 1996, Journal of Applied Physiology 81:643-652.

International Search Report and Written Opinion dated Apr. 22, 2022; International Application No. PCT/US2022/070101; 15 pages.

Katz, Eliot S., et al., "Genioglossus activity during sleep in normal control subjects and children with obstructive sleep apnea", Am J Respir Crit Care Med. Sep. 1, 2004;170(5):553-60 (Year: 2004).

* cited by examiner

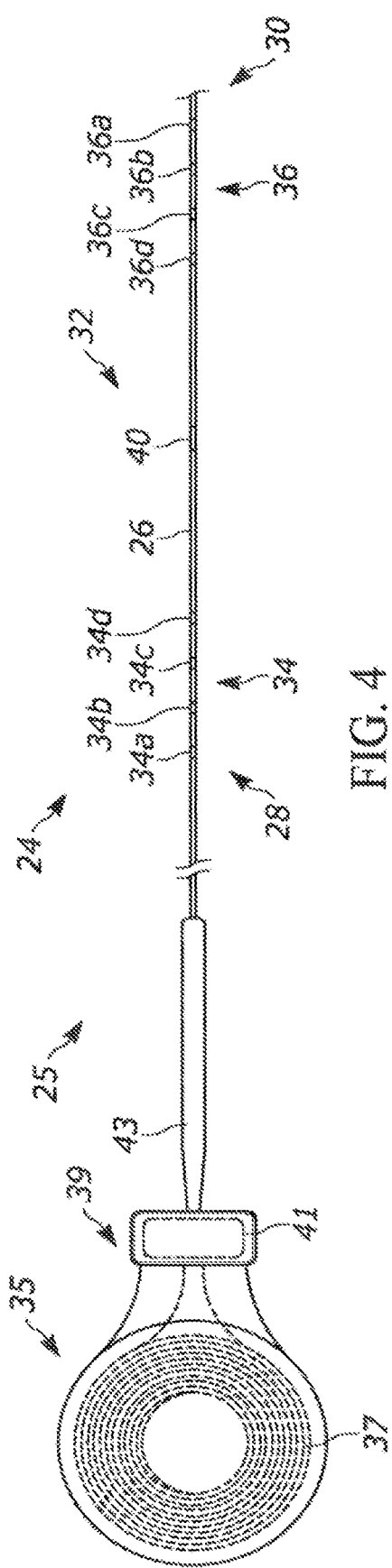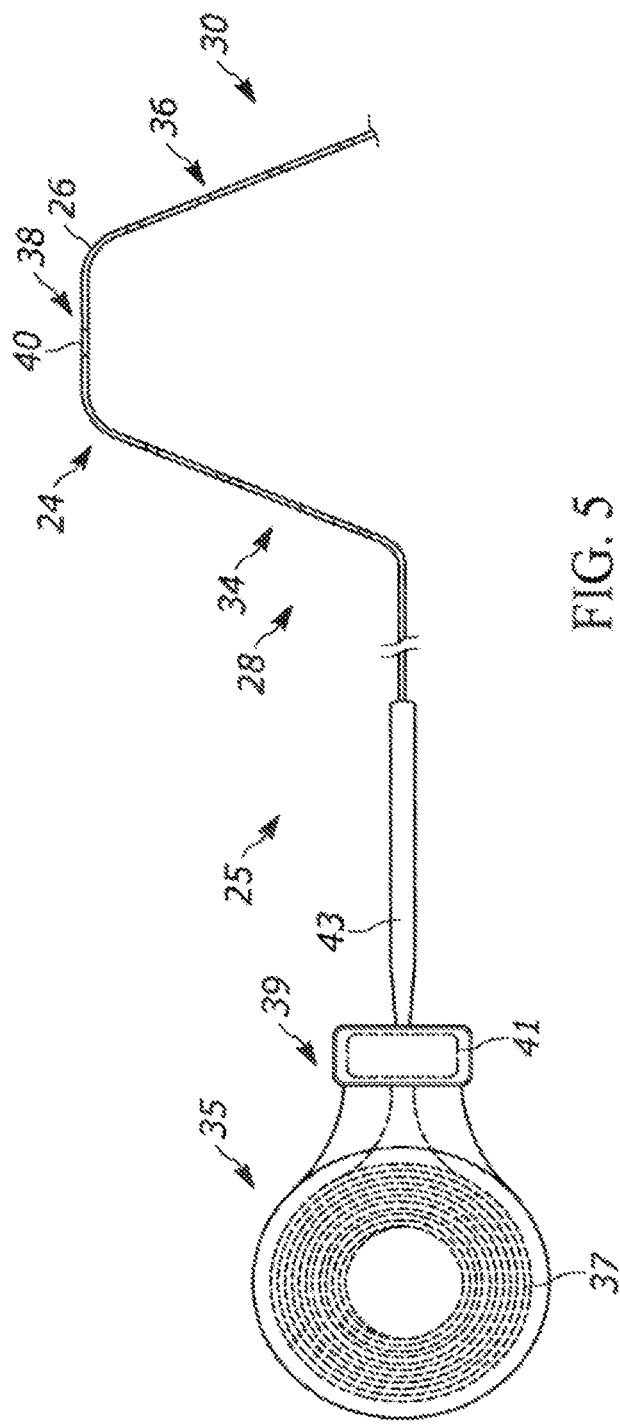
FIG. 4
FIG. 5

BIASED NEUROMODULATION LEAD AND METHOD OF USING SAME

CROSS-REFERENCE TO RELATED APPLICATIONS

The present application is a divisional of U.S. application Ser. No. 16/865,668, filed on May 4, 2020, which claims priority to U.S. Provisional Application No. 62/915,194, filed on Oct. 15, 2019, each of which is incorporated by reference herein in its entirety.

TECHNICAL FIELD

The present disclosure relates to a neuromodulation lead and method for treating sleep disordered breathing.

BACKGROUND

Upper airway sleep disorders (UASDs) or sleep disordered breathing (SDB) are conditions that occur in the upper airway that diminish sleep time and sleep quality, resulting in patients exhibiting symptoms that include daytime sleepiness, tiredness and lack of concentration. Obstructive sleep apnea (OSA), the most common type of UASD, is characterized by cessation of airflow because of upper airway obstruction despite simultaneous respiratory effort. The respiratory effort continues despite obstruction until the individual is aroused from sleep. During sleeping the genioglossus muscle and other muscles that hold the airway patent relax, causing the mandible and the tongue to move posteriorly, which decreases upper airway volume. The obstruction causes a decrease in oxygen blood level, leading to increased respiratory drive and this cycle continues until the patient is aroused.

OSA is highly prevalent, affecting one in five adults in the United States. One in fifteen adults has moderate to severe OSA requiring treatment. OSA is the most common type of sleep apnea. Untreated OSA results in reduced quality of life measures and increased risk of disease including hypertension, stroke, heart disease, etc. Continuous positive airway pressure (CPAP) is a standard treatment for OSA. While CPAP is non-invasive and highly effective, it is not well tolerated by all patients and has several side effects. Patient compliance and/or tolerance for CPAP is often reported to be between 40% and 60%. Surgical treatment options for OSA, such as anterior tongue muscle repositioning, orthognathic bimaxillary advancement, uvula-palatal-pharyngoplasty, and tracheostomy are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibular advancement), and/or they may be socially stigmatic (e.g., tracheostomy) and have extensive morbidity.

SUMMARY

Provided herein are neuromodulation leads and methods of treating SDB and other medical disorders. A neuromodulation lead can be used to stimulate the distal hypoglossal nerve trunk as well as distal branches of the hypoglossal nerve trunk that innervate the horizontal fibers and/or the oblique fibers within the genioglossus muscle as well as other muscles of the anterior lingual musculature. The application of stimulation to the hypoglossal nerve trunk and hypoglossal nerve distal fibers can enable airway maintenance during sleep for the treatment of SDB, such as obstructive sleep apnea (OSA). The neuromodulation lead can comprise a plurality of electrodes and can be configured or biased such that when positioned at the target site, such as between the geniohyoid and genioglossus muscles, the lead and the electrodes mirror the anatomy of the hypoglossal nerve bilaterally as the nerve approaches and starts to branch into the genioglossus muscle. In addition, or alternatively, the lead can be configured or biased to exert slight pressure on the genioglossus muscle and/or the hypoglossal nerve in an implanted configuration of the lead.

In an aspect, a neuromodulation lead is provided that comprises a lead body having a left portion, a right portion, and an intermediate portion therebetween. The lead body can be biased towards a substantially omega shape when fully deployed. The lead body can include a left set of electrodes disposed on the left portion of the lead body and a right set of electrodes disposed on the right portion of the lead body.

In another aspect, a neuromodulation lead is provided that comprises a lead body having a left portion, a right portion, and an intermediate portion therebetween. The lead body can be biased towards a substantially omega shape when fully deployed. The lead body can also include a left set of electrodes disposed on the left portion of the lead body and a right set of electrodes disposed on the right portion of the lead body. The location of the left and right set of electrodes on the respective left and right portion of the lead body can be based on the location of an electrical stimulation target site comprising the hypoglossal nerve trunk, distal branches of the hypoglossal nerve, nerve branches that innervate horizontal fibers within the genioglossus muscle, nerve branches that innervate oblique fibers within the genioglossus muscle, or suitable combinations thereof when the neuromodulation lead is fully deployed.

In another aspect, a neuromodulation lead is provided that comprises a lead body having a left portion, a right portion, and an intermediate portion therebetween. The lead body can include a left set of electrodes disposed on the left portion of the lead body and a right set of electrodes disposed on the right portion of the lead body. The intermediate portion can be biased towards an inferior position relative to the left and right electrode sets when the neuromodulation lead is fully deployed.

In another aspect, a method of treating SDB in a patient is provided. The method comprises obtaining a neuromodulation lead, positioning the neuromodulation lead between the geniohyoid muscle and the genioglossus muscle of the patient, and allowing the neuromodulation lead to assume a substantially omega shape within the plane between the geniohyoid muscle and the genioglossus muscle. The method can also include activating an electrode of the left set of electrodes, the right set of electrodes or both to apply an electrical signal to a target site to stimulate a nerve thereby treating the patient's SDB.

In another aspect, a method of treating SDB in a patient is provided. The method can comprise obtaining a neuromodulation lead comprising a lead body having a left portion, a right portion, and an intermediate portion therebetween. The lead can include a left set of electrodes disposed on the left portion of the lead body and a right set of electrodes disposed on the right portion of the lead body. The method can further include positioning the neuromodulation lead between the geniohyoid muscle and the genioglossus muscle of the patient and allowing the intermediate portion to assume an inferior position relative to the left and right electrode sets. The method can also include activating an electrode of the left set of electrodes, the right set of electrodes or both to apply an electrical signal to a target site to stimulate a nerve thereby treating the patient's SDB.

BRIEF DESCRIPTION OF DRAWINGS

FIG. 4 is a top view of a neuromodulation device in a non-deployed configuration according to an aspect of the present disclosure.

FIG. 5 is a top view of a neuromodulation device in a fully deployed configuration according to an aspect of the present disclosure. The neuromodulation lead can be inserted either from the left side or the right side of the patient.

DETAILED DESCRIPTION

As used herein with respect to a described element, the terms "a," "an," and "the" include at least one or more of the described elements including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration but can have a shape or configuration that is recognizable by one skilled in the art as generally or approximately having the described shape or configuration of the described element. As used herein, "stimulate" or "modulate" in the context of neuromodulation includes stimulating or inhibiting neural activity. A "patient" as described herein includes a mammal, such as a human being. By "improving," the patient's medical disorder is better after therapy than before therapy. As used herein, the terms, "inferior," "superior," "cranial," and caudal refer to anatomical planes and directions when the patient is in a standard anatomical position. Similarly, the terms "left" and "right" refer to the position of elements that correspond to the left and right side of a patient's body in a standard anatomical position.

Figure 1:
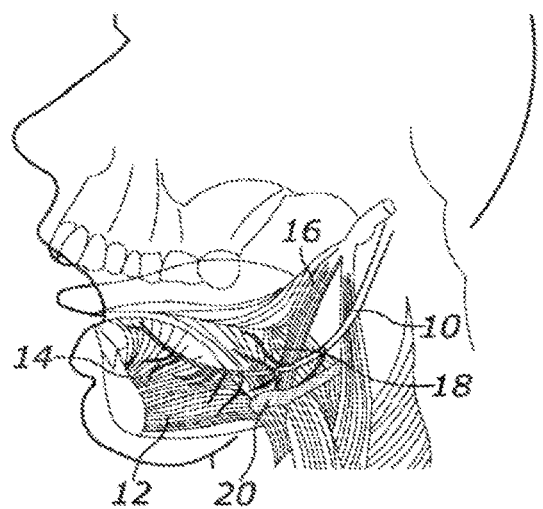
FIG. 1 is a cut-away lateral view of the anterior lingual musculature, the hypoglossal nerve and exemplary terminal branches thereof, and surrounding bony structure, including the mandible, of a human.
Figure 2:
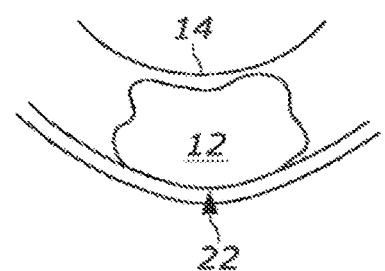
FIG. 2 is a schematic transverse view of the geniohyoid muscle, the genioglossus muscle and the mylohyoid muscle of a human with the mylohyoid muscle oriented inferiorly and the genioglossus muscle oriented superiorly.

By way of background and with reference to FIG. 1, the hypoglossal nerve 10 controls many upper airway muscles that affect airway patency. The hypoglossal nerve 10 innervates the geniohyoid muscle 12, the intrinsic muscles of the tongue, and the extrinsic muscles of the tongue, such as the genioglossus muscle 14, the styloglossus muscle 16, and the hyoglossus muscle 18. The genioglossus muscle and the geniohyoid muscles 14 and 12 are primary muscles involved in the dilation of the pharynx. As schematically illustrated in FIG. 2, the geniohyoid muscle 12 is situated superior to the mylohyoid muscle 22 and inferior to the genioglossus muscle 14. Contraction of the genioglossus muscle 14 can provide tongue protrusion, hence widening of the pharyngeal opening. Activation of the geniohyoid muscle 12 along with a tone present in the sternohyoid muscle can pull the hyoid bone 20 ventrally, thus again dilating the pharynx. On the other hand, the hyoglossus muscle 18 and the styloglossus muscle 16 are considered tongue retractor muscles. As such, the hypoglossal nerve has several branches as it courses toward the anterior lingual muscles, and specifically to the genioglossus muscle. The branches innervate both retruser and protruser muscles of the anterior lingual system. It is believed that effective treatment of SDB requires stimulation of the protruser muscles without activation of the retruser muscles. Thus, for neuromodulation therapy to be effective it is considered important to localize stimulation to the protruser muscles while avoiding activation of the retruser muscles.

Figure 3:
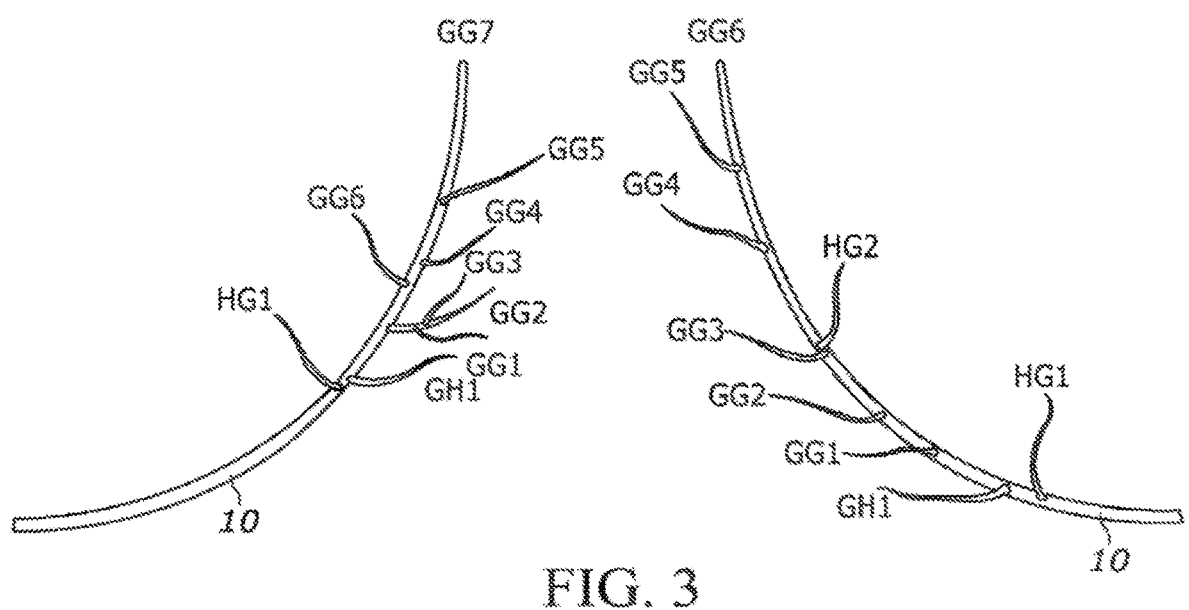
FIG. 3 is a schematic anterior depiction of an exemplary general arborization pattern and identification of the bilateral terminal branches of a hypoglossal nerve that innervate the genioglossus muscle (GG), the geniohyoid muscle (GH), and the hyoglossus muscle (HG) of a human. It should be noted that the hypoglossal nerve is illustrated as extending from the anterior mandible to the hyoid bone (i.e. from the top of the page to the bottom).

Referring back to FIG. 1 and as further schematically illustrated in FIG. 3, as the hypoglossal nerve 10 courses toward the anterior mandible, the first branches of the hypoglossal nerve 10 are branches that innervate the hyoglossus muscle (HG) and styloglossus muscles. The next branches of the hypoglossal nerve 10 are branches that innervate the geniohyoid (GH) and genioglossus (GG) muscles. In general, the number of branches varies individual to individual, but the course and direction of the branches are largely consistent individual to individual.

Although many methods of neuromodulating the anterior lingual muscles have been attempted, it is not known which branches are important to stimulate to achieve the desired efficacy for the treatment of SDB. It is believed that for treatment efficacy, a lead should be configured such that individual or small groups of individual branches can be activated as needed to achieve the desired effect.

A neuromodulation lead is provided herein that is configured to account for these and other considerations. In particular, a neuromodulation lead is provided that can be inserted and be positioned in the plane between the geniohyoid muscle and the genioglossus muscle. The neuromodulation lead can be configured to position electrodes along the nerve distribution of the hypoglossal nerve and its branches bilaterally. For example, and with reference to FIGS. 4 and 5, in an aspect, a neuromodulation lead 24 can comprise a lead body 26 having a left portion 28 comprising a left set of electrodes 34, a right portion 30 comprising a right set of electrodes 36, and an intermediate portion 32 therebetween. As described in more detail below, the electrodes can be used as stimulating electrodes to stimulate neural or neuromuscular tissue and/or as sensing electrodes to sense electrical activity, such as intrinsic or evoked electrical signals. Lead body 26 can be biased towards a substantially omega shape when fully deployed as shown in FIG. 5. In other words, lead body can be configured to transition from a substantially linear shape, as shown in FIG. 4, in a non-deployed state, such as during insertion, to a substantially omega shape, as shown in FIG. 5, when fully deployed. The neuromodulation lead is fully deployed when the neuromodulation lead is implanted in the patient's body and the electrodes are positioned at the desired locations in the patient's body. The omega shape of the neuromodulation lead can be created at the time of manufacturing such that the final form of the lead body is biased to have the omega shape, such bias being overcome if needed during insertion of the lead. The bias can be created, for example, by heat shaping or material shaping or other methods of manufacturing a biased lead. As stated above, the omega bias can allow the lead and the electrodes to mirror the anatomy of the hypoglossal nerve bilaterally as the nerve approaches and starts to branch into the genioglossus muscle.

A left set of electrodes 34 can be disposed on left portion 28 of lead body 26 and a right set of electrodes 36 can be disposed on right portion 30 of lead body 26. The electrodes can be used as stimulating electrodes. The electrodes can also be used as both stimulating and sensing electrodes for both stimulating target sites as well as sensing electrical activity, such as electromyogram activity, from the anterior lingual muscles. The electrodes can be ring electrodes extending substantially 360° about the lead body, for example, and can have substantially the same size as the target stimulation site(s). The electrodes can also be directional electrodes and not extend 360° about the lead body. Further, the electrodes can have electrode coatings to reduce the signal to noise ratio and/or allow for better long-term recording characteristics if used as sensing electrodes. If used as stimulating electrodes, an electrode coating can also allow the electrodes to have a larger charge injection profile for stimulation safety.

Figure 6:
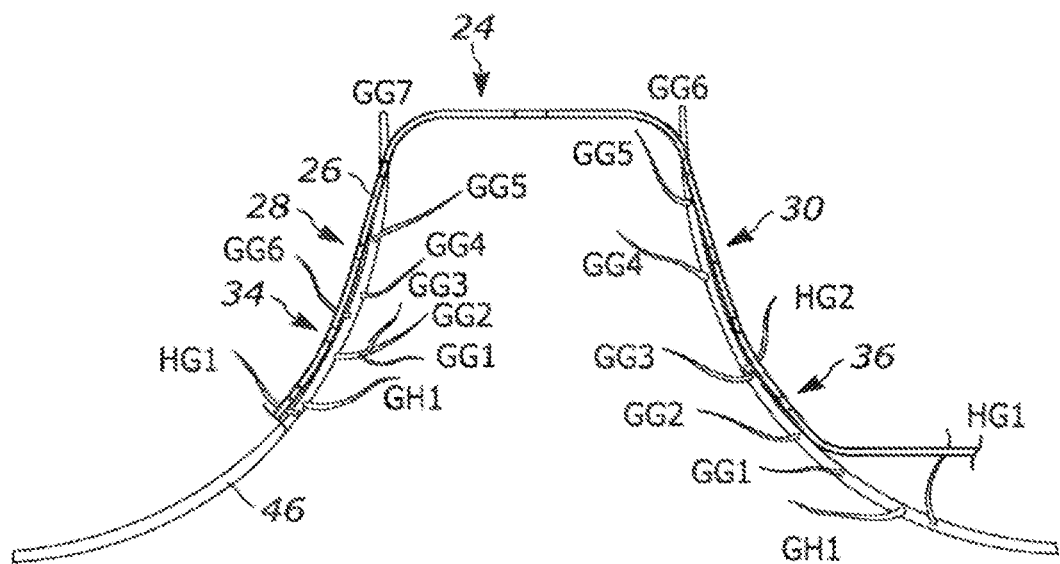
FIG. 6 is a schematic anterior view of a neuromodulation lead depicting the location of the electrodes on the lead body of the neuromodulation lead being adjacent to the location of distal branches of the hypoglossal nerve when the neuromodulation lead is fully deployed according to an aspect of the present disclosure. It should be noted that the hypoglossal nerve is illustrated as extending from the anterior mandible to the hyoid bone. (i.e. from the top of the page to the bottom)

Intermediate portion 32 of lead body 26 can define an apex 38 and an ultrasound marker 40 can be disposed at apex 38. As such, the neuromodulation lead can be inserted via ultrasound and ultrasound marker 40 can allow the user to identify when the apex of the neuromodulation lead is positioned at midline, allowing the electrode sets 34 and 36 to be positioned along the distribution of the hypoglossal nerve and its branches bilaterally as illustrated in FIG. 6. Ultrasound can also be used to track motion or potential dislodgment of the lead over time. One or more anchors can be disposed on the lead body to secure the neuromodulation lead in place. Such anchors can be hard or soft anchors, for example, including tines, barbs, prefabricated sutures, deployable anchors including time dependent deployable anchors (e.g., anchors that are polymer coated and deploy or release once the polymer dissolves), or combinations thereof.

The lead body can have different shapes. For example, the lead body can be cylindrical, flat or have an oval cross-sectional shape. The lead body can also have enlarged segments to allow for disposition of larger electrode pads or contacts thereon along the length of the lead.

FIGS. 4 and 5 also illustrate an exemplary neuromodulation device 25 comprising neuromodulation lead 24 and including an exemplary power receiver 35 that can be operably coupled to neuromodulation lead 24. Power receiver 35 can include a coiled receiver antenna 37 configured to produce an induced current in response to being disposed in an electromagnetic field. The antenna can comprise a substrate having an upper surface and a lower surface, an upper coil comprising a plurality of coil turns disposed on the upper surface of the substrate, and a lower coil comprising a plurality of coil turns disposed on the lower surface of the substrate. The upper and lower coils can be electrically connected to each other in parallel. In particular, advantageously, antenna 37 can implement a unique two-layer, pancake style coil configuration in which the upper and lower coils are configured in parallel. As a result, the upper and lower coils can generate an equal or substantially equal induced voltage potential when subjected to an electromagnetic field. This can help to equalize the voltage of the coils during use, and has been shown to significantly reduce the parasitic capacitance of antenna 37. In this parallel coil configuration of antenna 37, upper and lower can be shorted together within each turn. This design has been found to retain the benefit of lower series resistance in a two-layer design while, at the same time, greatly reducing the parasitic capacitance and producing a high maximum power output. Such an antenna is described in more detail in co-pending U.S. patent application Ser. No. 16/865,541, entitled: "Implantable Stimulation Systems, Devices and Methods" filed on May 4, 2020 which is incorporated by reference herein specifically, paragraphs [0043], [0044], and FIGS. 9A and 9B. Neuromodulation device 25 can further comprise electronics package 39 with one or more electronic components 41 mounted therein configured to control the application of stimulation energy via one or more of the electrodes. The antenna can be configured to supply electrical current to the electronics package to power the electronics package. The antenna can be constructed from a flexible circuit board and the upper and lower coils can be etched from conductive layers laminated onto the substrate of the antenna. The electronics package can comprise one or more electronic components mounted on a portion of the flexible circuit board, wherein the flexible circuit board is configured to electrically connect the one or more electronic components to the antenna. The neuromodulation device can include pigtail connector 43, which can extend from electronics package 39 and can facilitate connecting lead 24 to the electronics package. Pigtail connector 43 can facilitate a detachable connection between electronics package 39 and lead 24 so that leads of different configurations can be connected to the electronics package. This can facilitate manufacturing of the neuromodulation device. This can also allow a physician to select a lead having a desired size and/or configuration.

Additionally, the neuromodulation lead being separate from, and connectable to, the remainder of the neuromodulation device via a pigtail connector, can facilitate implanting the lead separately. As a result, implanting the lead can be much less invasive, allowing the lead to be placed via a small incision. An integrated design may necessitate a larger incision and also the need to handle and manipulate the entire neuromodulation device as a whole during the implantation process, which could complicate the lead placement, as the surgeon could have to work around the remainder of the neuromodulation device, e.g., the electronics package and the antenna.

Figure 7:
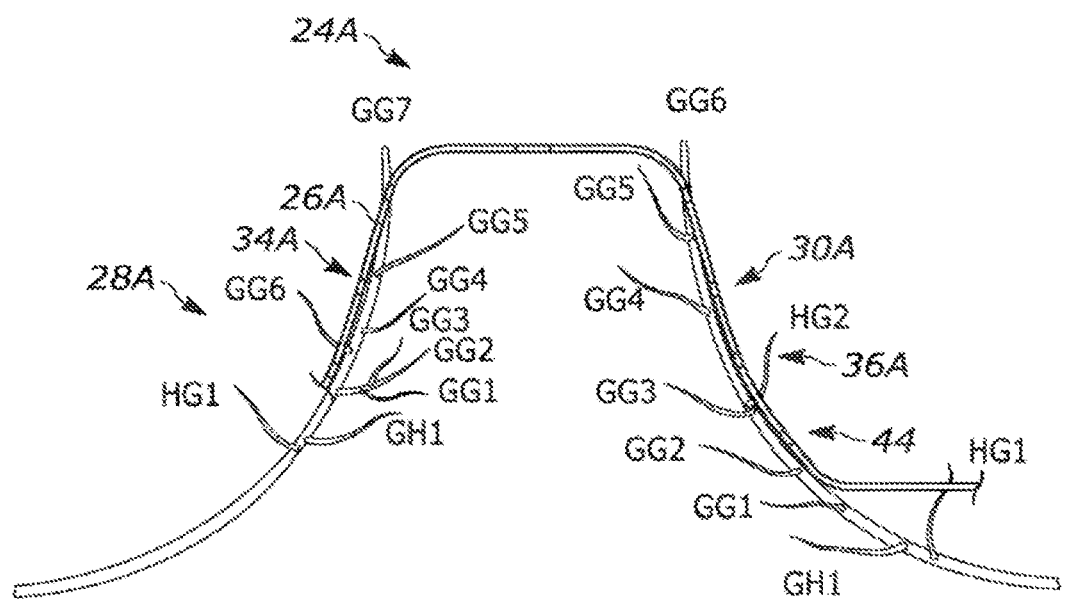
FIG. 7 is a schematic anterior view of a neuromodulation lead depicting the location of the electrodes on the lead body of the neuromodulation lead being adjacent to the location of distal branches of the hypoglossal nerve when the neuromodulation lead is fully deployed according to another aspect of the present disclosure. It should be noted that the hypoglossal nerve is illustrated as extending from the anterior mandible to the hyoid bone. (i.e. from the top of the page to the bottom)
Figure 8:
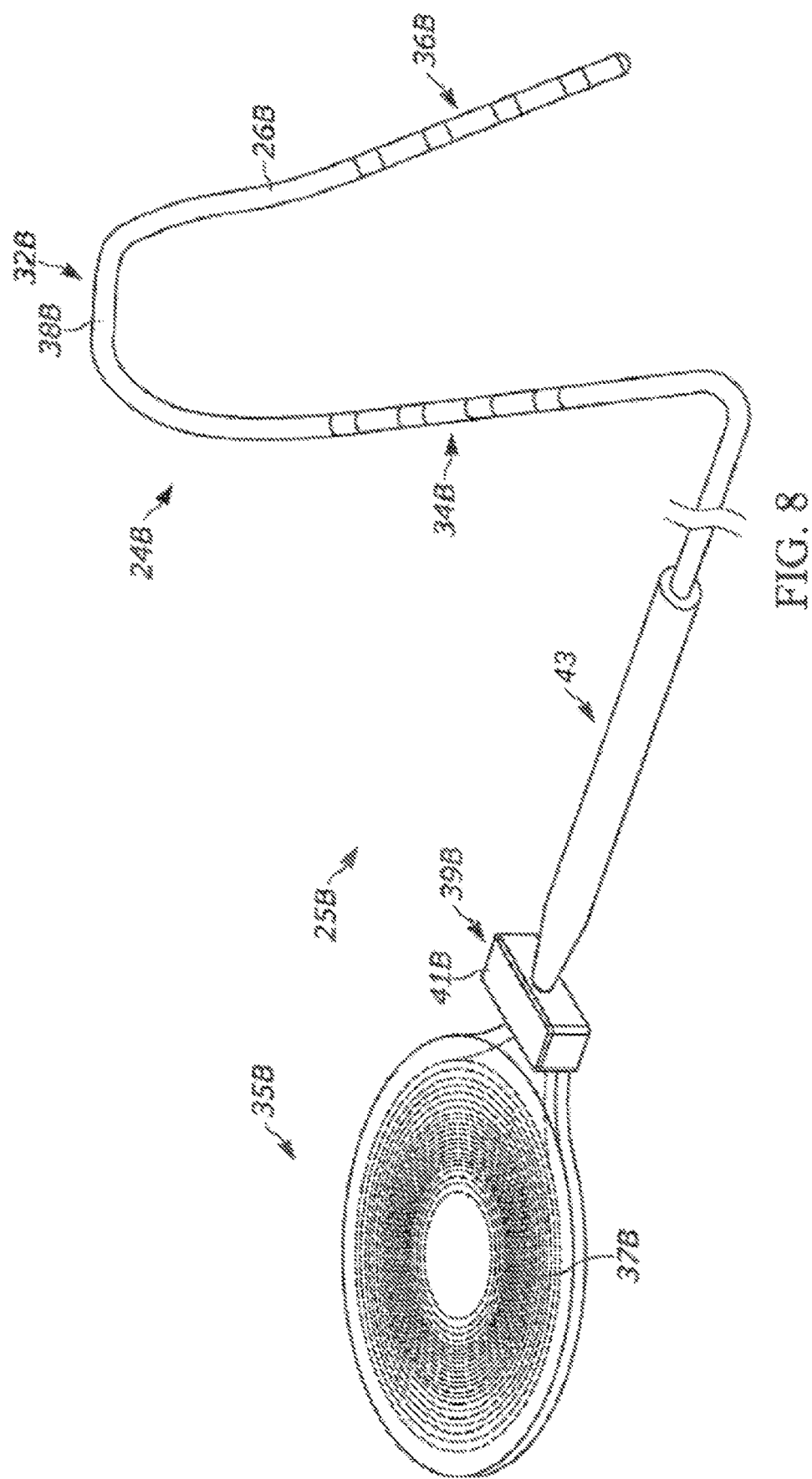
FIG. 8 is a perspective enlarged view of a neuromodulation device according to an aspect of the present disclosure.

As depicted in FIG. 6, the location of left and right set of electrodes 34 and 36 on the respective left and right portion 28 and 30 of lead body 26 can be based on the respective left and right location of a stimulation target site comprising the hypoglossal nerve trunk 46, distal branches of the hypoglossal nerve such as terminal branches that innervate the genioglossus muscle indicated by reference characters GG1 to GG7 or both when neuromodulation lead is fully deployed. It should be noted that the number of branches depicted in FIG. 6 and other similar figures is only exemplary as the number of branches can vary from individual to individual as stated above. Rather, FIGS. 6-8 are provided to depict the general location of the branches of the hypoglossal nerve. The location of the left and right set of electrodes on the respective left and right portion of the lead body can also be based on the respective left and right location of stimulation sites comprising nerve branches that innervate horizontal fibers within the genioglossus muscle, oblique fibers within the genioglossus muscle, or both when the neuromodulation lead is fully deployed.

As depicted in FIGS. 5 and 6, left set of electrodes 34 and right set of electrodes 36 can be symmetrically disposed on lead body 26. Alternatively, as depicted in FIG. 7, a neurostimulation lead 24A can comprise a lead body 26A where the left set of electrodes 34A and the right set of electrodes 36A are asymmetrically disposed on the lead body to avoid the hyoglossus muscle branches, for example. For instance, in an aspect, the electrode configuration of the lead can be such that an electrode is not aligned with a hyoglossus muscle branch when the lead is implanted whereas an electrode is disposed on a distal more section 44 of right portion 30A of lead body 26A. Such an embodiment can avoid stimulating the hyoglossus muscle branch HG1, for example, since the hyoglossus muscle is a retruser muscle and given that the location of the hyoglossus muscle branch can be different on the left side of the hypoglossal nerve of a patient compared to the right side of the hypoglossal nerve as illustrated in FIG. 7.

In certain aspects and with respect to FIG. 8 and FIGS. 10-15, when neuromodulation lead 24B is fully deployed, intermediate portion 32B of lead body 26B defining apex 38B can be located inferior/caudal to the left and right electrode sets 34B and 36B respectively. This can be seen in the inferior bend or bias of lead body 26B that leads into intermediate portion 32B. Such a bend or bias can allow the lead to exert upward or cranial pressure to press the electrodes against the genioglossal muscle and/or the hypoglossal nerve to allow for better contact between the electrode sets and the hypoglossal nerve and/or genioglossal muscle. In particular, this pressure is created by the intermediate portion, including the apex, being more caudal in the body and allowing the left and right portion of the lead body to be pushed more cranially into the genioglossus muscle. This bias allows for better contact with the genioglossus muscle, more lead stability and hence better long-term performance of the lead.

In particular, such a bias can reduce motion of the lead after encapsulation/scar tissue grows around the lead and thus allow for better contact between stimulating electrodes and the target stimulation sites as well as better contact between sensing electrodes and the muscle(s) from which electrical activity is sensed. The inferior bias can also reduce the amount of encapsulating tissue around the lead as well. This can improve the recording of electromyography (EMG) signals from muscles innervated by the hypoglossal nerve since the more encapsulating tissue around the sensing electrodes, the harder it can be to detect an EMG signal long term. As such, reduced motion of the lead and less encapsulation of tissue around the lead can result in better EMG recording as well as stimulation of target sites at lower stimulation thresholds and more consistent responses from stimulation over time.

Neuromodulation lead 24B can also be part of a neuromodulation device 25B that includes a power receiver 35B and electronics package 39B. Power receiver 35B can include a coiled receiver antenna 37B (exemplary aspects of which are described above).

Figure 9:
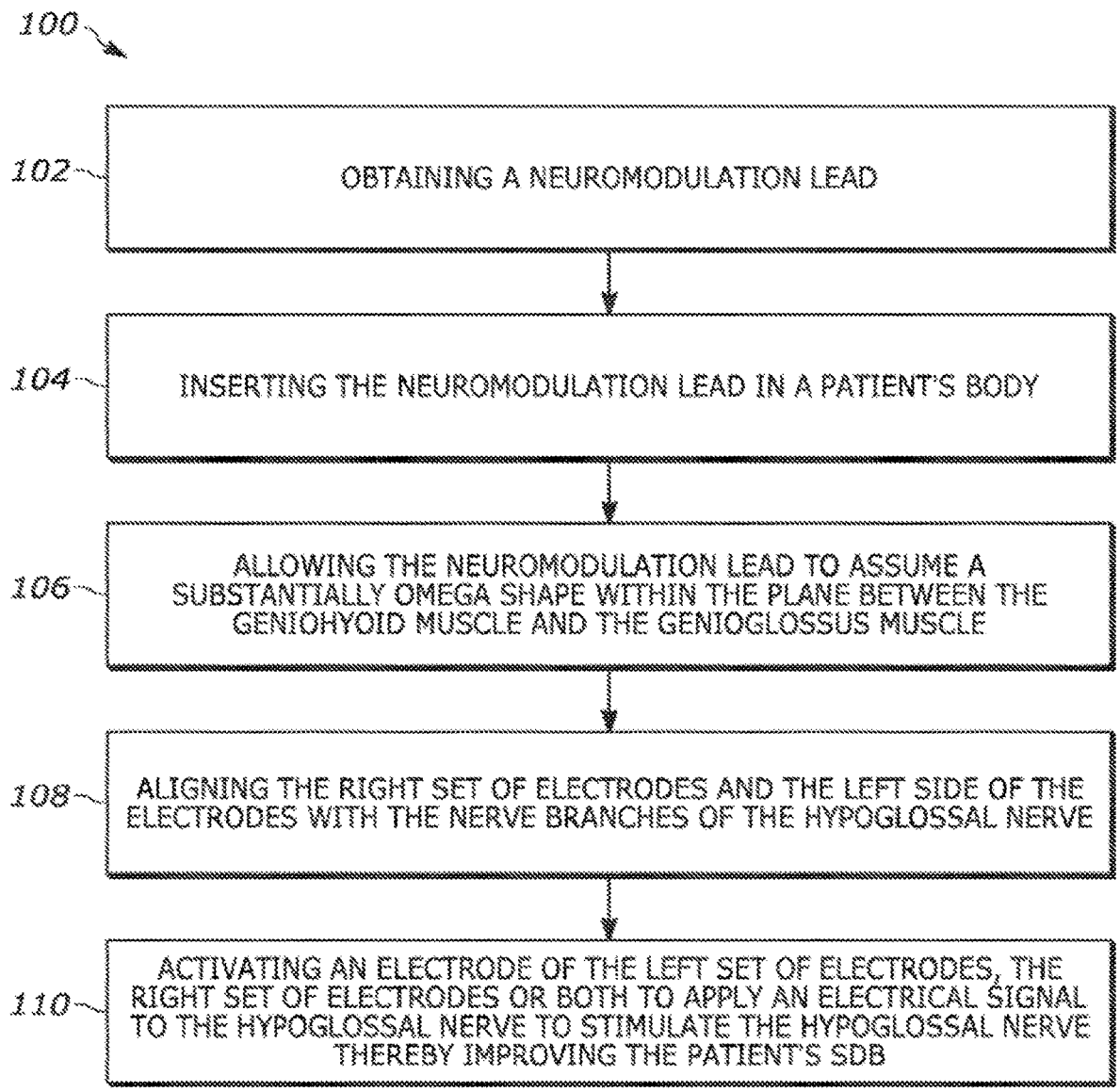
FIG. 9 is a flow diagram of exemplary steps of a method of treating sleep disordered breathing according to an aspect of the present disclosure.

Referring to FIG. 9 and with reference to FIGS. 10-15, a method of improving SDB or another disorder is also provided using a neuromodulation lead. Such a method 100 can comprise obtaining a neuromodulation lead 24B (102) comprising left and right electrodes 34B and 36B respectively. FIGS. 10-15 also illustrates an exemplary neuromodulation device 25B with a power receiver 35B including a coiled receiver antenna 37B that is operably coupled to neuromodulation lead 24B. Method 100 can include inserting the neuromodulation lead in a patient's body (104) and allowing the neuromodulation lead to assume a substantially omega shape within the plane between the geniohyoid muscle GH and the genioglossus muscle GG (106). The hypoglossal nerve (HGN) and its branches (HGN') are located in this plane bilaterally. Method 100 can further include aligning the right set of electrodes 36B and the left set of electrodes 34B with the nerve branches HGN' of the hypoglossal nerve HGN (108). Method 100 can then comprise activating an electrode of the right set of electrodes 36B, the left set of electrodes 36B or both to apply an electrical signal to the hypoglossal nerve HGN to stimulate the hypoglossal nerve HGN thereby improving the patient's SDB (110). The method can also include avoiding stimulating hyoglossus muscle branches, the styloglossus muscle branches, or both. Although the method outlined above is described with respect to the neuromodulation device depicted in FIG. 8, it is understood that other embodiments of a neuromodulation device and neuromodulation lead can be used in such methodology.

Regarding an exemplary method of implanting a neuromodulation device, such a method can comprise inserting a stylet about the neuromodulation lead or into a lumen of the neuromodulation lead such that the neuromodulation lead assumes a substantially linear shape.

The method can further include percutaneously inserting the neuromodulation lead in a patient's body under ultrasound guidance, for example. The method can then comprise positioning the neuromodulation lead, for example, between the geniohyoid muscle and the genioglossus muscle plane of the patient. The method can further include retracting the stylet to allow the neuromodulation lead to assume a substantially omega shape, for example, within the plane between the geniohyoid muscle and the genioglossus muscle. The method can then include activating an electrode of the left set of electrodes, the right set of electrodes or both to apply an electrical signal to a target site to stimulate the hypoglossal nerve, for example, thereby treating a medical disorder such as the patient's SDB. The target site can be, for example, a hypoglossal nerve trunk, distal branches of the hypoglossal nerve, horizontal fibers within an anterior lingual muscle, oblique fibers within an anterior lingual muscle, or combinations thereof. The method can also include avoiding stimulating hyoglossus muscle branches, the styloglossus muscle branches, or both.

With respect to a specific exemplary percutaneous method of implantation, an insertion tool can be used to create a percutaneous puncture through the skin and subcutaneous tissue below the skin. When at the right depth, the insertion tool can create a curved path such that insertion of the neuromodulation lead does not penetrate into the genioglossus muscle but remains within the plane between the geniohyoid muscle and the genioglossus muscle. When positioned correctly, a small instrument can be deployed into the muscle plane and then swept anteriorly and posteriorly in line with the muscle plane to create a small space for the neuromodulation lead to be deployed between the geniohyoid muscle and the genioglossus muscle. Such steps can involve soft, blunt dissection of the muscle plane and not dissection of the muscle fibers. For example, a balloon dissection tool having a pre-configured balloon geometry can be inflated and cause separation between the muscles using gentle pressure. Once space is made for the neuromodulation lead, the small instrument can be retracted and the neuromodulation lead can be deployed. The lead can be deployed across midline, allowing the operator to visualize a midline ultrasound marker. Once positioned correctly, the neuromodulation lead can be deployed by removing the stiffener around or inside the lead, allowing the neuromodulation lead to take its natural omega shape, all within the plane between the geniohyoid and genioglossus. The insertion tool can be removed and the proximal end of the neuromodulation lead can be exposed through the skin.

Figure 10:
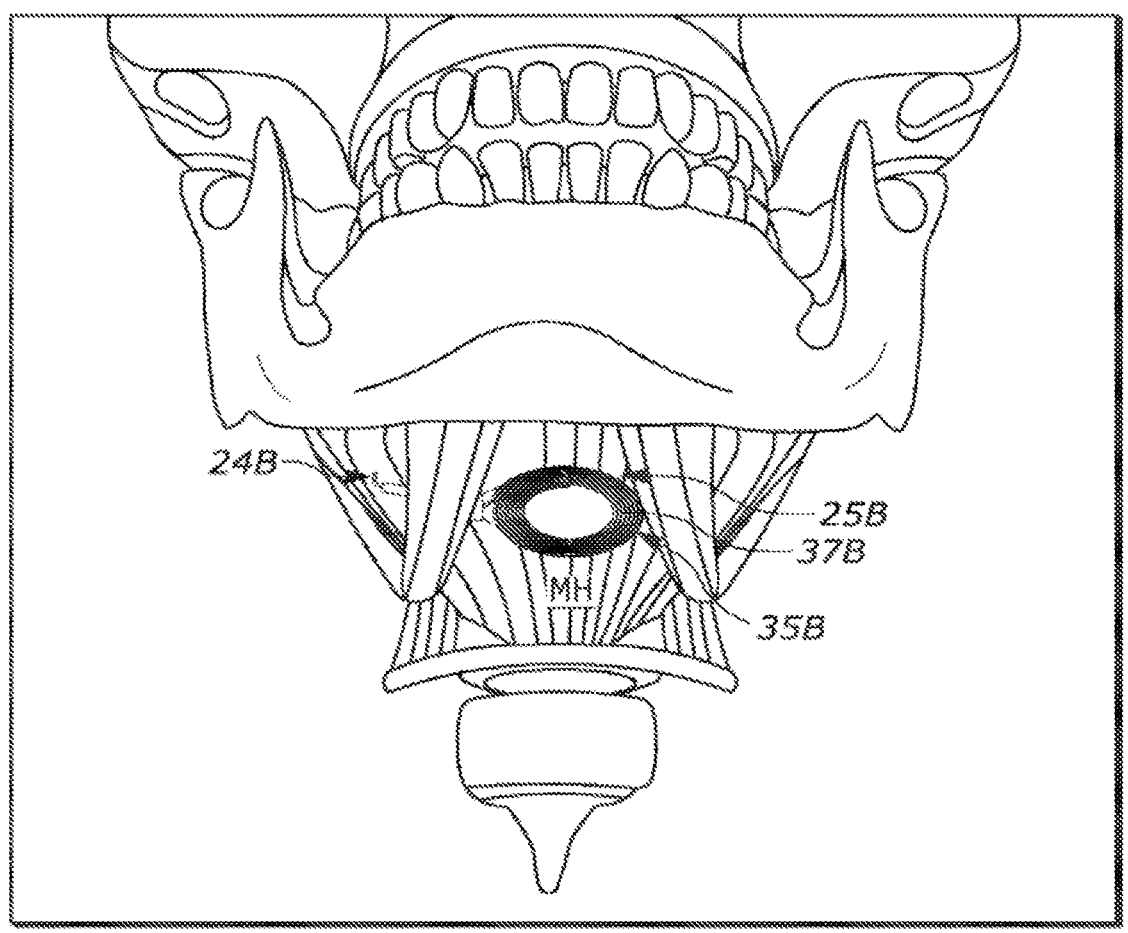
FIGS. 10-15 are schematic illustrations of different views of a neuromodulation device implanted in a patient identifying anterior lingual musculature, the hypoglossal nerve including branches thereof, and surrounding anatomical structures.
Figure 11:
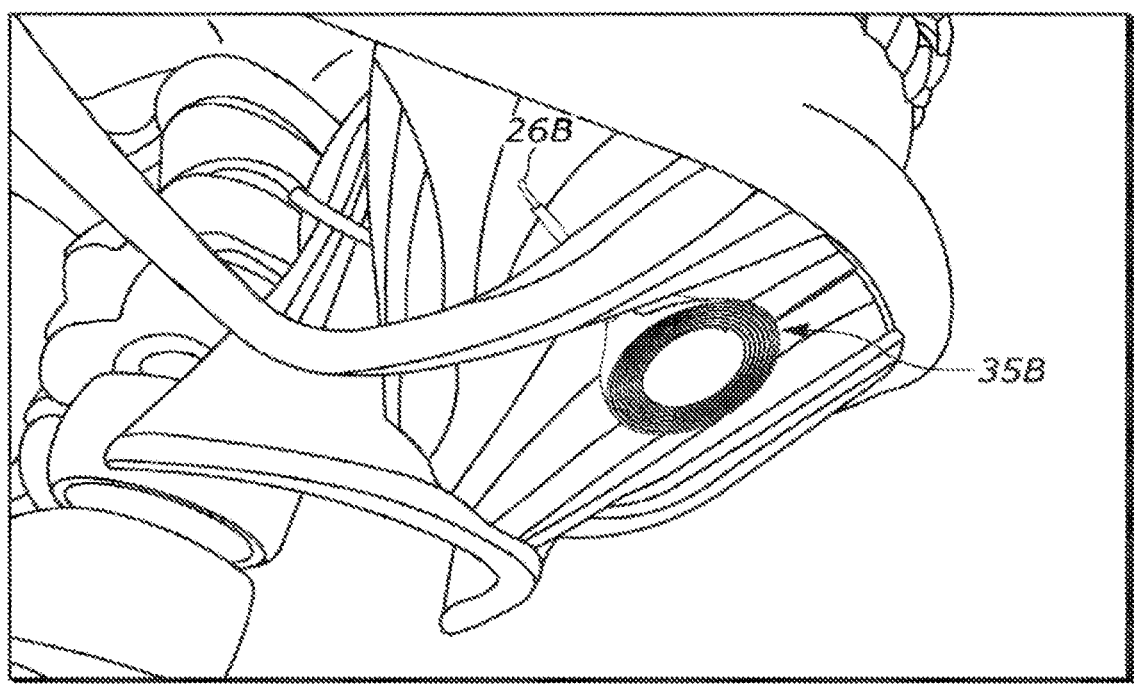
Figure 12:
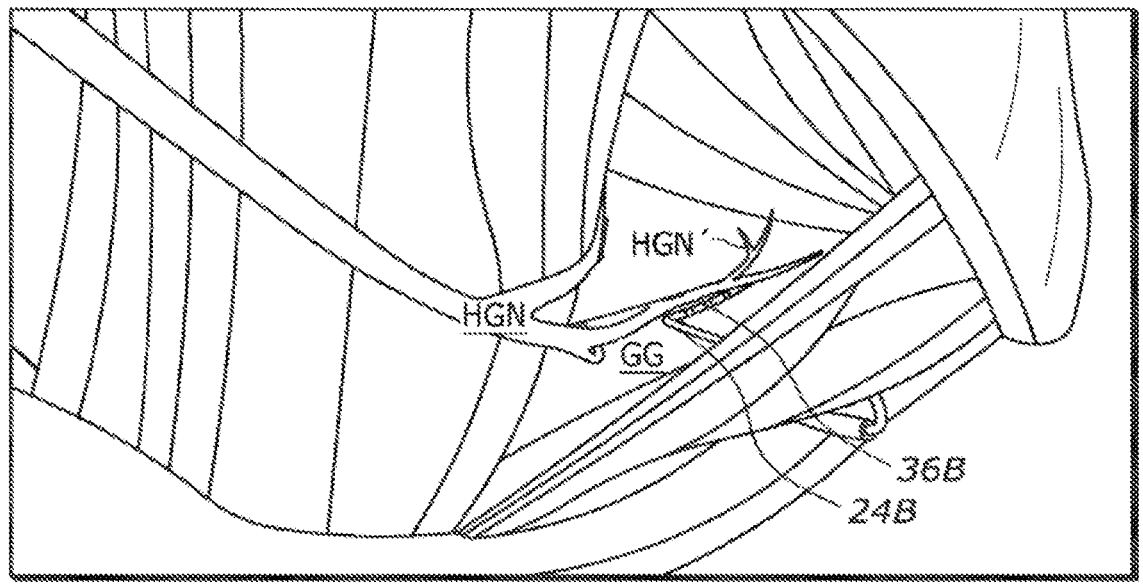
Figure 13:
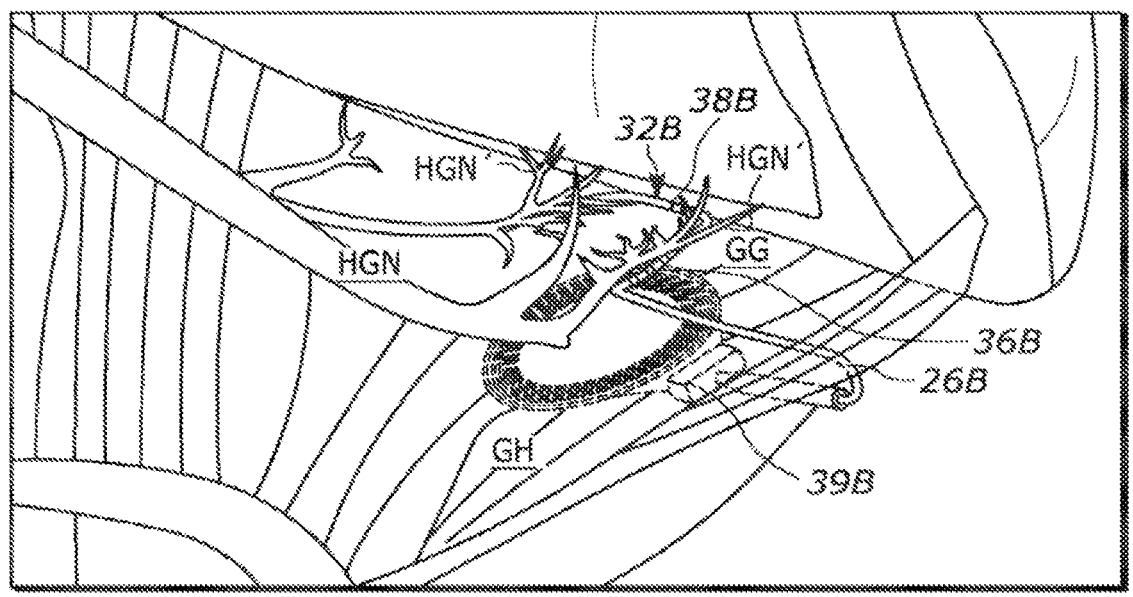
Figure 14:
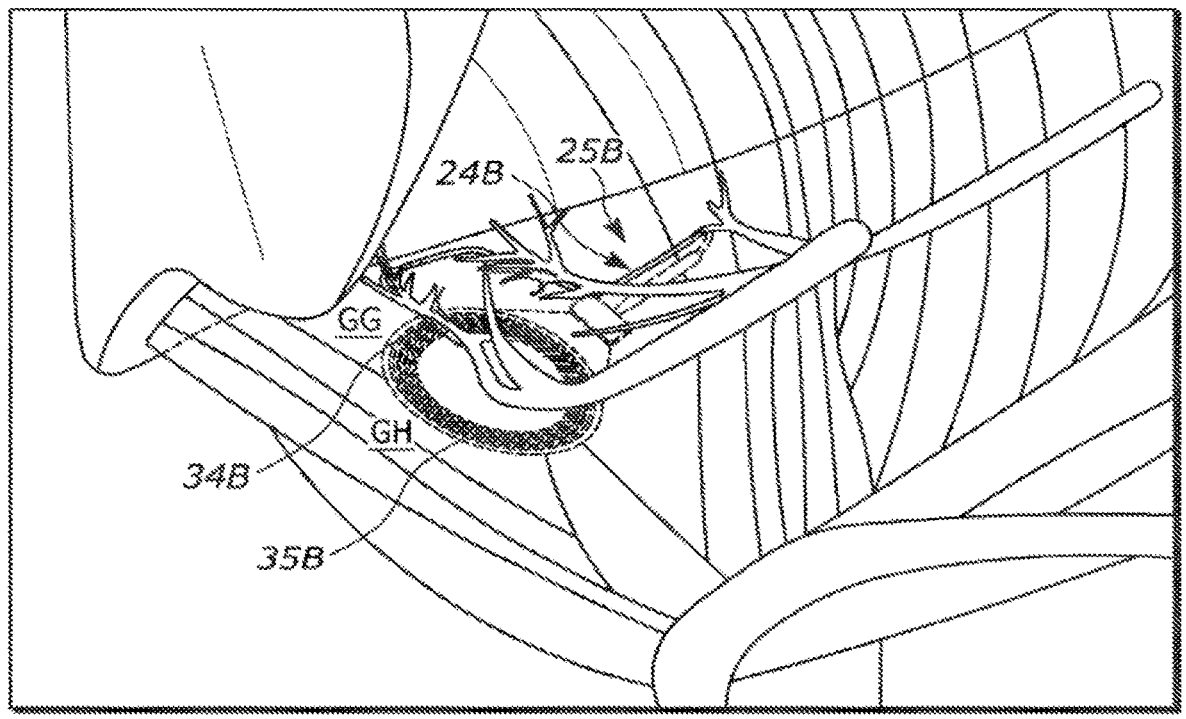
Figure 15:
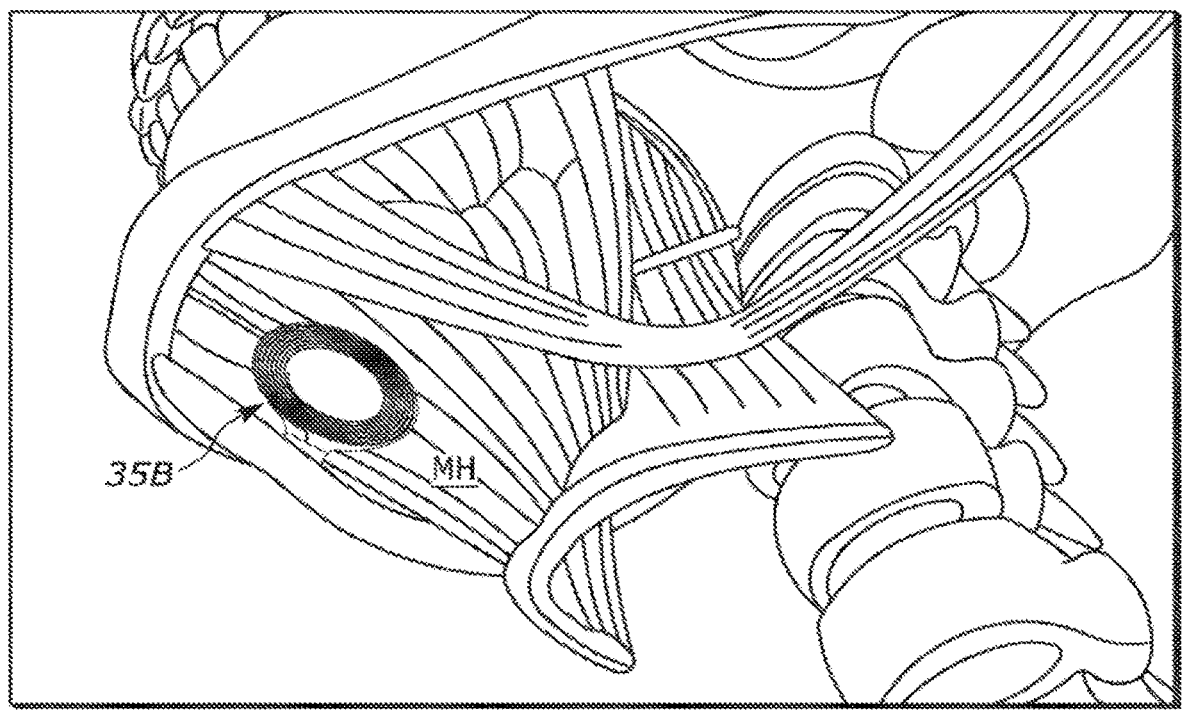
Figure 16:
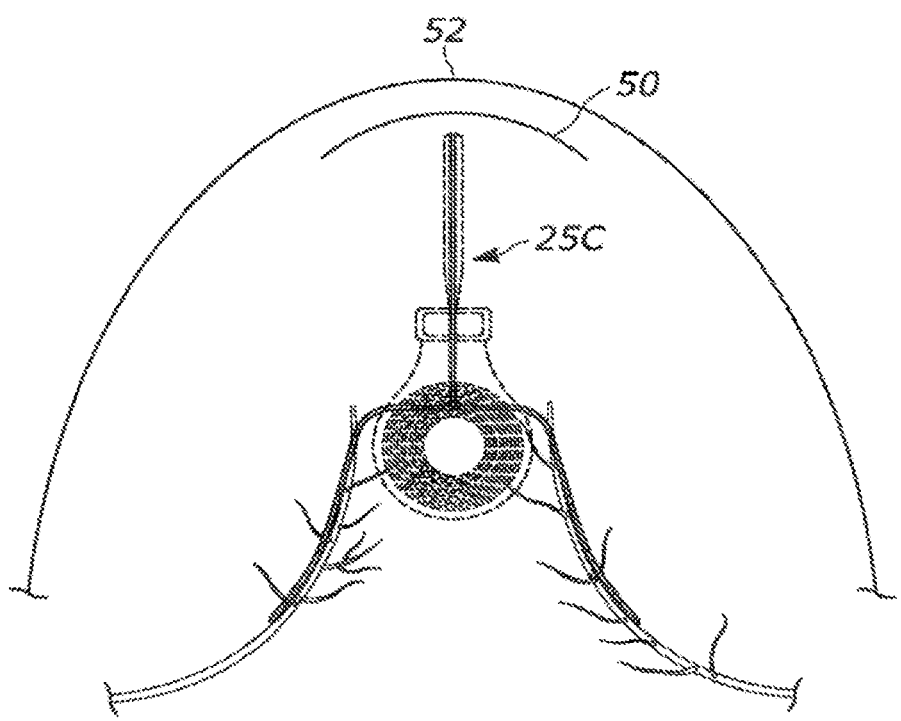
FIG. 16 is a transverse view of a neuromodulation device implanted in a patient identifying an illustrative incision and implantation site.

With reference to FIGS. 10 and 16, another exemplary non-percutaneous method of implanting a neuromodulation device 25C uses a "pull along" lead approach instead of a stylet. Instead of using ultrasound and a percutaneous approach, such a surgical approach can utilize a small incision and dissection to allow visualization of the surgical plane in which the neuromodulation lead 24C is inserted. The procedure can start with approximately a 1.5 centimeter (cm) to 2 cm transverse incision 50 in the chin 52 fold (e.g., a sub-malar incision). This incision can be directed through the skin and subcutaneous fat and then, dissecting through the platysma muscle and sub-platysma fat, the digastric muscles (left and right) can be located and the muscle raphe of the mylohyoid muscle (MH) can be identified. Using standard techniques, the mylohyoid raphe can be dissected and the surface of the geniohyoid muscle and its midline raphe can be identified. Again, using standard techniques, the raphe of the geniohyoid can be dissected through to expose a small portion (e.g., approximately 1 cm) of the plane between the geniohyoid muscle and the genioglossus muscle. This plane can be identified by the midline and lateral fat pads that surrounds the nerves and vascular that innervate the anterior lingual muscles (e.g., geniohyoid, genioglossus and others). These fat pads are where the hypoglossal nerve trunk and branches are localized.

Then a small curved needle can be inserted just medial to the jaw line and just anterior to the mandibular notch where the facial artery runs. The needle can be inserted with a medial and posterior approach, so that the tip of the needle enters into the plane exposed with the surgical dissection, e.g., the plane between the geniohyoid and genioglossus muscles. The needle can be inserted into the plane at the caudal border of the exposure and cross midline exiting the plane in a lateral direction. The needle can then exit the skin contralaterally to the original insertion location. The needle can be attached to the neuromodulation lead using a connector, such as a suture. The needle can be pulled through to allow the neuromodulation lead to enter the surgical plane. The connector can be removed and the position of the neuromodulation lead can be adjusted so that the electrodes align with the fat pads and the nerve branches of the hypoglossal nerve. The proximal end of neuromodulation lead can be exposed at the original insertion point and that proximal end can be connected to the electronic package and power receiver once the power receiver antenna coil is implanted. In particular, the power receiver antenna can be implanted in a caudal direction from the original transverse chin fold incision. The power receiver antenna can be implanted deep to the digastric muscles on top of the mylohyoid muscle (MH). Once the power receiver antenna is placed, the proximal end of the neuromodulation lead (via a connector, for example) can be tunneled to the power receiver antenna and connected. The muscle planes and the skin can be closed to complete the insertion.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

We claim:

1. A method of treating sleep disordered breathing (SDB) in a patient, the method comprising:
    placing a distal portion of a neuromodulation lead between a geniohyoid muscle and a genioglossus muscle of the patient, wherein the distal portion of the neuromodulation lead comprises a left portion having a left set of electrodes, a right portion having a right set of electrodes, and an intermediate portion therebetween;
    aligning the left set of electrodes and the right set of electrodes with left nerve branches and right nerve branches of a hypoglossal nerve, respectively; and
    positioning a proximal portion of the neuromodulation lead folded over itself such that the distal portion of the neuromodulation lead at least partially overlaps with an antenna that is coupled to the proximal portion of the neuromodulation lead.

2. The method of claim 1, wherein placing the neuromodulation lead comprises placing the neuromodulation lead such that the intermediate portion of the lead is located caudal to the left and right portions of the neuromodulation lead.

3. The method of claim 2, wherein placing the neuromodulation lead comprises placing the neuromodulation lead such that the left and right portions of the neuromodulation lead are pressed cranially into the genioglossus muscle via a bias in the neuromodulation lead.

4. The method of claim 1, wherein aligning the left set of electrodes and the right set of electrodes comprises aligning the left portion of the neuromodulation lead and the right portion of the neuromodulation lead with the left nerve branches and the right nerve branches of the hypoglossal nerve, respectively.

5. The method of claim 1, further comprising performing an incision in a chin fold of the patient and exposing a portion of a plane between the geniohyoid muscle and the genioglossus muscle.

6. The method of claim 1, wherein at least one of the left set of electrodes and the right set of electrodes comprises at least one stimulating electrode.

7. The method of claim 6, wherein the at least one stimulating electrode in the placed neuromodulation lead is configured to stimulate a target stimulation site comprising at least one of a hypoglossal nerve trunk, a distal branch of the hypoglossal nerve, a nerve branch that innervates horizontal fibers within the genioglossus muscle, and a nerve branch that innervates oblique fibers within the genioglossus muscle.

8. The method of claim 1, wherein at least one electrode of the left set of electrodes and the right set of electrodes is usable as a sensing electrode.

9. The method of claim 8, wherein the at least one sensing electrode is configured to sense electromyography (EMG) signals.

10. The method of claim 1, wherein the neuromodulation lead comprises one or more anchors.

11. The method of claim 10, wherein the one or more anchors comprises one or more tines, barbs, prefabricated sutures, deployable anchors, or a combination thereof.

12. The method of claim 1, wherein the antenna is configured to produce an induced current in response to being disposed in an electromagnetic field.

13. The method of claim 1, wherein the SDB is sleep apnea.

14. The method of claim 1, further comprising positioning the antenna on a surface of a mylohyoid muscle of the patient.

15. A method of treating sleep disordered breathing in a patient, the method comprising:
- placing a neuromodulation lead between a geniohyoid muscle and a genioglossus muscle of the patient, wherein the neuromodulation lead comprises a distal portion comprising a left portion having a left set of electrodes, a right portion having a right set of electrodes, and an intermediate portion therebetween;
- aligning the left set of electrodes and the right set of electrodes with left nerve branches and right nerve branches of a hypoglossal nerve, respectively;
- positioning the intermediate portion of the neuromodulation lead inferior to the left and right sets of electrodes, such that the intermediate portion pushes the left and right sets of electrodes further cranially into the genioglossus muscle; and
- positioning a proximal portion of the neuromodulation lead folded over itself such that the distal portion of the neuromodulation lead at least partially overlaps with an antenna that is coupled to the proximal portion of the neuromodulation lead.

16. The method of claim 15, wherein positioning the intermediate portion of the neuromodulation lead comprises positioning the intermediate portion outside of a plane along which the left and right sets of electrodes are oriented.

17. The method of claim 16, wherein the neuromodulation lead comprises a preformed bend that biases the intermediate portion away from the plane.

18. The method of claim 15, wherein aligning the left set of electrodes and the right set of electrodes comprises aligning the left portion of the neuromodulation lead with the left nerve branches of the hypoglossal nerve and aligning the right portion of the neuromodulation lead with the right nerve branches of the hypoglossal nerve.

19. The method of claim 15, wherein at least one of the left set of electrodes and the right set of electrodes comprises at least one stimulating electrode.

20. The method of claim 19, further comprising stimulating, with the at least one stimulating electrode, a target stimulation site comprising at least one of a hypoglossal nerve trunk, a distal branch of the hypoglossal nerve, a nerve branch that innervates horizontal fibers within the genioglossus muscle, and a nerve branch that innervates oblique fibers within the genioglossus muscle.

21. The method of claim 20, further comprising avoiding stimulating a hyoglossus muscle branch, a styloglossus muscle branch, or both with the left and right sets of electrodes.

22. The method of claim 15, wherein at least one electrode of the left set of electrodes and the right set of electrodes is usable as a sensing electrode.

23. The method of claim 22, wherein the at least one sensing electrode is configured to sense electromyography (EMG) signals.

24. The method of claim 23, further comprising sensing EMG signals from one or more muscles innervated by the hypoglossal nerve.

25. The method of claim 15, wherein the neuromodulation lead comprises one or more anchors.

26. The method of claim 25, wherein the one or more anchors comprises one or more tines, barbs, prefabricated sutures, deployable anchors, or a combination thereof.

27. The method of claim 15, wherein the antenna is configured to produce an induced current in response to being disposed in an electromagnetic field.

28. The method of claim 15, further comprising performing an incision in a chin fold of the patient and exposing a portion of a plane between the geniohyoid muscle and the genioglossus muscle.

29. The method of claim 15, wherein the sleep disordered breathing comprises sleep apnea.

* * * * *

UNITED STATES PATENT AND TRADEMARK OFFICE
CERTIFICATE OF CORRECTION

| | | |
|---|---|---|
| PATENT NO. | : 11,883,667 B2 | Page 1 of 1 |
| APPLICATION NO. | : 17/660042 | |
| DATED | : January 30, 2024 | |
| INVENTOR(S) | : Caparso et al. | |

It is certified that error appears in the above-identified patent and that said Letters Patent is hereby corrected as shown below:

On the Title Page

Item (72), Inventors, Line 2:
Delete "Louisville, KY (US)" insert -- Louisville, KY (US); Ryan Soose, Pittsburgh, PA (US) --, therefor.

Signed and Sealed this
Twenty-eighth Day of January, 2025

Coke Morgan Stewart
*Acting Director of the United States Patent and Trademark Office*